United States Patent [19]

Dietrich et al.

[11] 4,049,681

[45] Sept. 20, 1977

[54] PROCESSES FOR THE SEPARATION OF POTASSIUM SALTS OF PERFLUOROALKANOIC ACIDS FROM AQUEOUS SOLUTIONS THEREOF

[75] Inventors: Peter Dietrich; Gunter Engler, both of Berlin; Armin Ferse; Harald Grimm, both of Dresden; Udo Gross, Berlin; Klaus Lunkwitz, Dresden; Dietrich Prescher, Berlin; Jürgen Schulze, Berlin; Astrid Wallbraun, Berlin, all of Germany

[73] Assignee: Akademie der Wissenschaften der D D R, Berlin-Adlershof, Germany

[21] Appl. No.: 641,919

[22] Filed: Dec. 18, 1975

[51] Int. Cl.$^2$ .......................... C09F 7/00; C11C 3/00
[52] U.S. Cl. ................. 260/408; 260/412.8; 260/419; 260/428.5; 260/539 R
[58] Field of Search ............... 260/408, 539 R, 412.8, 260/419, 428.5

[56] References Cited

U.S. PATENT DOCUMENTS

| | | | |
|---|---|---|---|
| 2,802,028 | 8/1957 | England | 260/408 X |
| 2,831,004 | 4/1958 | Barnhart et al. | 260/408 |
| 2,863,889 | 12/1958 | Marks | 260/408 |
| 2,948,741 | 8/1960 | Barnhart et al. | 260/408 |
| 3,542,859 | 11/1970 | Litt | 260/408 X |
| 3,816,524 | 6/1974 | Grinstead | 260/539 R |
| 3,882,153 | 5/1975 | Seki et al. | 260/408 |

Primary Examiner—Winston A. Douglas
Assistant Examiner—John F. Niebling
Attorney, Agent, or Firm—Michael J. Striker

[57] ABSTRACT

Processes for the separation of a potassium salt of a perfluoroalkanoic acid having at least 1 and at most 12 carbon atoms per molecule or a mixture of potassium salts of a homologous mixture of the said perfluoroalkanoic acids from an aqueous solution that also contains a substantial proportion of one or more watersoluble salts of inorganic acids which process comprises extracting at room temperature the said aqueous solution with an organic solvent which is at least partially miscible with water and in which potassium salts of the said perfluoroalkanoic acids are soluble, the said organic solvent being selected from the group consisting of alkanols having at least 3 and at most 5 carbon atoms per molecule, ketones having at least 3 and at most 7 carbon atoms per molecule, N,N-dimethylformamide and dimethyl sulfoxide, and subsequently recovering the potassium salt of the perfluoroalkanoic acid or mixture of potassium salts of the homologous mixture of perfluoroalkanoic acids.

13 Claims, No Drawings

PROCESSES FOR THE SEPARATION OF POTASSIUM SALTS OF PERFLUOROALKANOIC ACIDS FROM AQUEOUS SOLUTIONS THEREOF

BACKGROUND OF THE INVENTION

The present invention pertains to processes for the separation of potassium salts of perfluoroalkanoic acids having at least 1 and at most 12 carbon atoms per molecule from aqueous solutions thereof.

As used herein the term "perfluoroalkanoic acids" refers to acyclic monocarboxylic acids all or most of the hydrogen atoms of which have been replaced by fluorine, such as, for example, trifluoroacetic, heptafluorobutyric, perfluorooctanoic, and similar acids.

Heretofore alkali-metal salts of perfluoroalkanoic acids such as are formed by hydrolysis of esters, nitriles, and acyl fluorides of such acids in aqueous alkaline media have been recovered from such aqueous solutions by evaporating the said solutions to dryness and extracting the dry residue with ethanol. This process has the disadvantage that the extraction must be performed in the absence of water with absolute (anhydrous) ethanol since inorganic salts readily dissolve in aqueous ethanol.

In another known process, the perfluoroalkanoic acid is extracted from an aqueous acidic medium with diethyl ether. This process has the disadvantage that it is not adapted for the separation of lower perfluoroalkanoic acids since these lower acids form hydrates which cannot be separated or can be separated only with difficulty by distillation from diethyl ether and other organic solvents or by other methods, such as by drying over phosphorus pentoxide. The amount of water that is carried over in distillation can be very high. Heptafluorobutyric acid, for example, forms an azeotrope which contains 72% by weight of water and only 28% by weight of the acid.

In the case of homologous mixtures of perfluoroalkanoic acids, but not perfluoroalkanoic acids of uniform chain length, it is moreover a condition of an extraction process that all perfluoroalkanoic acids or their salts have essentially the same solubility in the extractant, regardless of their chain length. The solubility in water of potassium salts of perfluoroalkanoic acids, for example, increases substantially with decreasing chain length so that as a rule liquid-liquid extraction with an organic solvent of these salts from an aqueous solution thereof can only be accomplished with difficulty.

Furthermore, processes have also been described for the extraction of individual perfluoroalkanoic acids. Besides the perfluoroalkanoic acids that are produced, inorganic fluorides or other salts are formed therewith so that a complete separation of the foreign salts from the desired salt of the perfluoroalkanoic acid is not achieved.

In the case of mixtures of inorganic salts and salts of perfluoroalkanoic acids with a wider range of chain lengths, the extraction of the dry residue of the evaporated solution does not produce a complete separation since the inorganic salts are also partially soluble in the extractants.

On the other hand, to separate free perfluoroalkanoic acids that are contaminated with accompanying inorganic acids, either by extraction or distillation, leads ultimately to corrosion of the extraction or distillation apparatus.

SUMMARY OF THE INVENTION

The principal object of the present invention is to provide a process for effectively separating at a minimal cost a potassium salt of a perfluoroalkanoic acid or potassium salts of a homologous mixture of perfluoroalkanoic acids having at least 1 and at most 12 carbon atoms per molecule from a mixture containing the said potassium salts as well as salts of inorganic acids. This object is accomplished in accordance with the present invention by a process which involves a simple liquid-liquid extraction step.

It has been discovered that potassium salts of perfluoroalkanoic acids having at least 1 and at most 12 carbon atoms per molecule and potassium salts of homologous mixtures of such acids can be extracted at room temperature from concentrated aqueous solutions containing higher concentrations of salts of inorganic acids with organic solvents that are at least partially miscible with water and in which the potassium salts of the perfluoroalkanoic acids are soluble. It was quite surprising that, when such solvents as lower alkanols having at least 3 and at most 5 carbon atoms per molecule, ketones having at least 3 and at most 7 carbon atoms per molecule, N,N-dimethyl-formamide and dimethyl sulfoxide, which are normally at least partially miscible with water, they were almost completely insoluble in the aqueous phase of the mixture under the conditions prevailing in the process. Isopropanol is an especially suitable solvent or extractant for this purpose.

The separation can be effected most advantageously when the aqueous solution before contact with the extractant is concentrated, for example, by evaporation to such a degree that it is saturated and crystals start to form and separate therefrom.

Extractants that were found to be especially suitable for separating the potassium salts of perfluoroalkanoic acids from aqueous solutions that also contain water-soluble salts of inorganic acids in accordance with the processes of the present invention are alkanols, preferably isopropanol; ketones, for example, acetone and methyl ethyl ketone, and strongly polar solvents such as N,N-dimethylformamide and dimethyl sulfoxide. The solubility of the extractant in the aqueous solution is reduced by the water-soluble salt of the organic acid that is dissolved therein which prevents the extractant from itself dissolving therein. In case the amount of the potassium salt of the perfluoroalkanoic acid in the queous solution is greater than the amount of the salt of the inorganic acid, the amount of the latter should be increased before the extractant is brought into contact with the aqueous solution in order to obtain an optimal extraction of the potassium salt of the perfluoroalkanoic acid.

DETAILED DESCRIPTION AND PREFERRED EMBODIMENTS OF THE INVENTION

The invention is described further in connection with the examples which follow, which were selected solely for purposes of illustration and consequently are not to be construed as limitative of the invention or its scope.

COMPARATIVE EXAMPLE

To a solution of 40 grams of pure potassium fluoride in 100 milliliters of distilled water was added 100 milliliters of isopropanol and the mixture was vigorously shaken for 10 minutes in a shaking machine. The isopropanol phase was then separated therefrom. This operation was repeated with a second 100-milliliter portion of isopropanol and the two extracts were combined and evaporated to dryness and the residue was weighed. In this manner, 0.12 gram of potassium fluoride, equivalent to 0.3% of the original quantity, was obtained.

EXAMPLE 1

In the same manner as described in the comparative example hereinbefore, a solution of 40 grams of potassium fluoride and 15 grams of potassium trifluoroacetate ($KOOC-CF_3$) in 100 milliliters of water was extracted twice with isopropanol. The residue after evaporation of the extracts weighed 11.23 grams, which is equivalent to 74.9% of the original quantity of potassium trifluoroacetate.

EXAMPLE 2

In the same manner as described in the comparative example hereinbefore, a solution of 20 grams of potassium fluoride and 5.3 grams of potassium tetrafluorobutyrate ($KOOC-C_3F_7$) in 50 milliliters of water was extracted twice with milliliters of isopropanol. The residue after evaporation of the extracts weighed 5.2 grams, which is equivalent to 98% of the original quantity of potassium heptafluorobutyrate.

EXAMPLE 3

An aqueous solution containing potassium fluoride and potassium perfluoroalkanoic acids that was obtained by introducing a statistically distributed mixture of perfluoroalkanoic acid fluorides having from 1 to 12 carbon atoms per molecule into an aqueous 4-molal solution of potassium hydroxide was evaporated on a water bath in an open tray until crystals began to separate in the boiling liquid. After cooling the solution, it was extracted twice with equal volumes of isopropanol and the extracts were combined and evaporated to dryness, leaving 29 grams of residue.

Subsequently the aqueous phase that had been extracted with isopropanol was evaporated to dryness and the residue, consisting of potassium bicarbonate, potassium carbonate and potassium fluoride, were subjected to infrared absorption spectral analysis. The residue was found to be free of potassium salts of perfluoroalkanoic acids, which was confirmed by the absence of both absorption bands at 1160 $cm^{-1}$ and 1240 $cm^{-1}$ that are characteristic of the C-F band, indicating that all of the potassium salts of the perfluoroalkanoic acids had been extracted in the isopropanol.

EXAMPLES 4 to 7

In each of the examples which follow, 8 grams of a mixture of potassium salts of a homologous mixture of perfluoroalkanoic acids having from 1 to 12 carbon atoms per molecule was added to an aqueous solution of 40 grams of potassium fluoride in 100 milliliters of water. This solution was then extracted twice with 100 milliliters of an organic solvent by vigorously shaking the mixture in a shaking machine for a period of 10 minutes and the organic phase was then separated, evaporated to dryness, and weighed.

The following amounts of potassium salts of perfluoroalkanoic acids were thus recovered with the solution was extracted with each of the following solvents:

Example 4: Isopropanol 7.2 grams; 90% recovery.
Example 5: n-butanol 6.2 grams; 77.5% recovery.
Example 6: Methyl ethyl ketone 6.0 grams; 76.3% recovery.
Example 7: N,N-Dimethylformamide 5.3 grams; 66.3% recovery.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A process for the separation of a potassium salt of a perfluoroalkanoic acid having at least 1 and at most 12 carbon atoms per molecule or a mixture of potassium salts of a homologous mixture of the said perfluoroalkanoic acids from an aqueous solution that also contains a substantial proportion of one or more water-soluble salts of inorganic acids, which process comprises extracting at room temperature the said aqueous solution with an organic solvent that is at least partially miscible with water and in which potassium salts of the said perfluoroalkanoic acids are soluble, the said organic solvent being selected from the group consisting of alkanols having at least 3 and at most 5 carbon atoms per molecule, ketones having at least 3 and at most 7 carbon atoms per molecule, N,N-dimethylformamide, and dimethyl sulfoxide, and subsequently recovering the potassium salt of the perfluoroalkanoic acid or mixture of potassium salts of the homologous mixture of perfluoroalkanoic acids from the extract.

2. A process as defined in claim 1 in which the solubility of the organic solvent in the aqueous solution is reduced by the water-soluble salt of the inorganic acid that is dissolved therein.

3. A process as defined in claim 1 in which the water-soluble salt of the inorganic acid is potassium fluoride.

4. A process as defined in claim 1 in which the initial amount of the water-soluble salt of the inorganic acid is greater than the initial amount of the potassium salt or salts of perfluoroalkanoic acid or acids.

5. A process as defined in claim 1 in which the organic solvent is isopropanol.

6. A process as defined in claim 1 in which the organic solvent is n-butanol.

7. A process as defined in claim 1 in which the organic solvent is methyl ethyl ketone.

8. A process as defined in claim 1 in which the organic solvent is N,N-dimethylformamide.

9. A process as defined in claim 1 in which the organic solvent is dimethyl sulfoxide.

10. A process as defined in claim 1 which comprises adding a mixture of perfluoroalkanoic acid fluorides having at least 1 and at most 12 carbon atoms per molecule to an aqueous solution of potassium hydroxide, evaporating the said solution until crystals start to form therein, cooling the said solution to room temperature, then extracting the said solution with isopropanol, and recovering the potassium salts of perfluoroalkanoic acids from the said extract.

11. A process for the separation of a potassium salt of a perfluoroalkanoic acid having at least 1 and at most 12 carbon atoms per molecule or a mixture of potassium salts of a homologous mixture of the said perfluoroalkanoic acids from an aqueous solution that also contains a substantial proportion of one or more water-soluble salts of inorganic acids, which process comprises extracting at room temperature the said aqueous solution with an organic solvent that is at least partially miscible with water and in which potassium salts of the said perfluoroalkanoic acids are soluble, the said organic solvent being selected from the group consisting of alkanols having at least 3 and at most 5 carbon atoms per molecule, ketones having at least 3 and at most 5 carbon atoms per molecule, N,N-dimethylformamide, and dimethyl sulfoxide, and subsequently recovering the potassium salt of the perfluoroalkanoic acid or mixture of potassium salts of the homologous mixture of perfluoroalkanoic acids from the extract.

12. A process for the separation of a potassium salt of a perfluoroalkanoic acid having at least 1 and at most 12 carbon atoms per molecule or a mixture of potassium salts of a homologous mixture of the said perfluoroalkanoic acids from an aqueous solution that also contains a substantial proportion of one or more water-soluble salts of inorganic acids, which process comprises removing the potassium salts of said perfluoroalkanoic acids by extracting at room temperature the said aqueous solution with a polar organic solvent under non-acidic conditions, said organic solvent being at least partially miscible with water and in which potassium salts of the said perfluoroalkanoic acids are soluble, the said organic solvent being selected from the group consisting of alkanols having at least 3 and at most 5 carbon atoms per molecule, ketones having at least 3 and at most 7 carbon atoms per molecule, N,N-dimethylformamide, and dimethyl sulfoxide, and subsequently recovering the potassium salt of the perfluoroalkanoic acid or mixture of potassium salts of the homologous mixture of perfluoroalkanoic acids from the extract.

13. A process for the separation of a potassium salt of a perfluoroalkanoic acid having at least 1 and at most 12 carbon atoms per molecule or a mixture of potassium salts of a homologous mixture of the said perfluoroalkanoic acids from an aqueous solution that also contains a substantial portion of one or more water-soluble salts of inorganic acids, which process comprises extracting at room temperature the said aqueous solution with a polar organic solvent under non-acidic conditions, said organic solvent being at least partially miscible with water and in which potassium salts of the said perfluoroalkanoic acids are soluble, the said organic solvent being selected from the group consisting of alkanols having at least 3 and at most 5 carbon atoms per molecule, ketones having at least 3 and at most 5 carbon atoms per molecule, N,N-dimethylformamide, and dimethyl sulfoxide, and subsequently recovering the potassium salt of the perfluoroalkanoic acid or mixture of potassium salts of the homologous mixture of perfluoroalkanoic acids from the extract.

* * * * *